(12) United States Patent
Dreschel et al.

(10) Patent No.: US 6,605,043 B1
(45) Date of Patent: Aug. 12, 2003

(54) DIAGNOSTIC MEDICAL ULTRASOUND SYSTEMS AND TRANSDUCERS UTILIZING MICRO-MECHANICAL COMPONENTS

(75) Inventors: William R. Dreschel, State College; Terry Kling, Port Matilda, both of PA (US); John W. Sliwa, Los Altos; Stuart L. Carp, Menlo Park, both of CA (US)

(73) Assignee: Acuson Corp., Mountain View, CA (US)

( * ) Notice: Subject to any disclaimer, the term of this patent is extended or adjusted under 35 U.S.C. 154(b) by 0 days.

(21) Appl. No.: 09/223,257

(22) Filed: Dec. 30, 1998

Related U.S. Application Data
(60) Provisional application No. 60/109,122, filed on Nov. 19, 1998.

(51) Int. Cl.[7] .................................................. A61B 8/01
(52) U.S. Cl. ..................................................... 600/459
(58) Field of Search ............................... 600/443, 433, 600/459, 447, 444, 461, 438; 357/26, 51; 361/283

(56) References Cited

U.S. PATENT DOCUMENTS

| | | | |
|---|---|---|---|
| 4,262,399 A | 4/1981 | Cady ......................... 29/25.42 |
| 4,432,007 A | * 2/1984 | Cady ............................ 357/26 |
| 5,415,175 A | 5/1995 | Hanafy et al. ......... 128/662.03 |
| 5,438,998 A | 8/1995 | Hanafy ................... 128/662.03 |
| 5,479,042 A | 12/1995 | James et al. ............. 257/415 |
| 5,582,177 A | 12/1996 | Hanafy et al. ......... 128/662.03 |
| 5,619,476 A | 4/1997 | Haller et al. | |
| 5,651,365 A | 7/1997 | Hanafy et al. ......... 128/662.03 |
| 5,701,901 A | 12/1997 | Lum et al. ................... 600/463 |
| 5,724,976 A | 3/1998 | Mine et al. ............. 178/662.03 |
| 5,743,855 A | 4/1998 | Hanafy et al. .............. 600/459 |
| 5,744,898 A | * 4/1998 | Smith et al. ................ 310/334 |
| 5,760,530 A | 6/1998 | Kolesar ...................... 310/339 |
| 5,792,058 A | 8/1998 | Lee et al. .................... 600/459 |
| 5,870,351 A | * 2/1999 | Ladabaum et al. ......... 367/163 |
| 5,876,345 A | 3/1999 | Eaton et al. ................ 600/466 |
| 5,894,452 A | 4/1999 | Ladabaum et al. | |
| 5,982,709 A | 11/1999 | Ladabaum et al. | |
| 6,004,832 A | * 12/1999 | Haller et al. ................... 438/50 |
| 6,251,074 B1 | 6/2001 | Averkiou et al. ........... 600/447 |
| 6,328,697 B1 | * 12/2001 | Fraser ......................... 600/459 |

OTHER PUBLICATIONS

Roger Grace Associates market projection for the MEMS market (http://www.rgraceassoc.com/com_mems.html).

"Electrostatically actuated micromechanical switches using surface micromachining", Prof. Paul M. Zavracky, Ph.D., http://www.ece.neu.edu/edsnu/zavracky/mfl/programs/relay/relay.html.

Shuvo Roy, http://mems.cwru.edu/roy/roy.html/. http://mems.cwru.edu/roy/content_guide.html, http://mems.cwru.edu/roy/projects/microrelays.html, http://mems.cwru.edu/roy/publications.html, http://mems.cwru.edu/roy/pix/relayc.gif.

Ezekiel J. J. Kruglick, Project Overview: Micro–Relays, http://www–bsac.eecs.berkeley.edu/~kruglick/relays/ relays.html.

Technical Report on Microactuated Resettable Switch, TiNi Alloy Company, http://quark.plk.af.mil/abstracts/97/TR-971005.html.

(List continued on next page.)

*Primary Examiner*—Marvin M. Lateef
*Assistant Examiner*—Mawlin Patel

(57) ABSTRACT

The use of any micro-mechanical component in an ultrasound system is disclosed. In particular, the use of micro-relays, micro-switches and inductors in the transducer probe head, in the transducer connector, coupled with the system transducer connector(s) or anywhere else in the system. In an ultrasound system, micro-mechanical components such as micro-fabricated switches, relays and inductors permit impressive size reduction, cost reduction, signal-integrity enhancement and improved operational flexibility.

59 Claims, 5 Drawing Sheets

OTHER PUBLICATIONS

Low–Power, High–Performance MEMS–based Switch Fabric, North Carolina State University, http://ece.ncsu.edu/erl/damemi/switchproj.html.

MAFET Thrust 3: A Revolutionary Program for Solid–State RF Power Generation and Control, E. R. Brown, http://web–ext2.darpa.mil/ETO/MAFET/thrust3/Thrust3Paper.html.

IC MEMS Microtransducers, H. Baltes, et al, http://www.iqe.ethz.ch/~baltes/ic_mems/ic_mems.html.

"Fully integrated magnetically actuated micromachined relays" by W. Taylor et al appearing in the Journal of Microelectromechanical Systems, Jun. 1, 1998, v7 n2, p181.

"Characteristics of micro–mechanical electrostatic switch for active matrix displays" by T. Nishio et al appearing in IEICE Transactions on Electronics, Sep. 1, 1995, v78, n9, p1292.

"Micromachined Capacitive Transducer Arrays for Medical Ultrasound Imaging" X.C. Jin, F. L. Degertekin, S. Calmes X. J. Zhang, I Ladabaum, B. T. Khuri–Yakub (Stanford)(1998 IEEE Conference in Sendai).

"Novel Silicon Nitride Micromachined WIde Bandwidth Ultrasonic Transducers" R. A. Noble, R. J. Robertson, D. R. Billlson, D. A. Hutchins (University of Warwick) (1998 IEEE Conference in Sendai).

"Surface Micromachined Capacitive Ultrasonic Transducers" Igal Ladabaum, Xuecheng Jin, Hyongsok T. Soh, Abdullah Atalar, Butrus T. Khuri–Yakub (IEEE Trans. Ultra. Ferro. Freq. Ctl vol. 45, No. 3, May 1998).

WWW Pages for Shuvo Roy, MEMS Research Group, obtained at internet address http://mems.cwru.edu/roy/roy.html/, jttp://mems,cwru.edu/roy/contenthuede.html. http://mems.cwru.edu/roy/projects/microrelays.html, http://mems.cwru.edu/roy/publications.html, http://mems.cwru.edu/pix/relayc.gif, Dec. 31, 1998.

Ezekiel J.J. Kruglick and Professor Kristofer S.J. Pister, Project Overview: Micro–Relays, obtained at internet address *http://www–bsac.eecs.berkeley.edu/~kruglick/relays.html*pp. 1–2, Dec. 31, 1998.

Technical Report Abstract on Microactuated Resettable Switch, TINI Alloy Company, obtained at internet address *http://quark.plk.af.mil/abstracts/97/TR971005.html*, Dec. 31, 1998.

Low–Power, High–Performance MEMS–based Switch Fabric (From a presentation to DARPA) by Paul D. Franzon, North Carolina State University, obtained at internet address *http://ece.ncsu.edu/erl/damemi/switchproj.html*, Feb. 9, 1999.

Mafet Thrust 3: A Revolutionary Program for Solid–State RF Power Generation and Control, E.R. Brown, Obtained at internet address *http://web–ext2.darpa.mil/ETO/MAFET/thrust3/Paper.html*, pp. 1–9, Dec. 31, 1998.

IC MEMS Microtransducers, H. Baites, et al, obtained at internet. address *http://www.iqe/ethz.ch/~baltes/icmems.html*, pp. 1–15, Dec. 31, 1998.

"MEMS Technology Pursued For The Development of Micromachined Silicon Variable Inductors and Latching Accelerometers", appearing in Electronic Design, Jun. 23, 1997, pp. 27–32.

"Fully integrated magnetically actuated micromachined relays" by W. Taylor et al. appearing in the Journal of Microelectromechanical Systems, Jun. 01, 1998, v7, n2, p. 181.

"Characteristics of micromechanical electrostatic switch for active matrix displays" by T. Nishio et al., appearing in IEICE Transactions on Electronics Sep. 1, 1995, v78, n9, p. 1292.

"Micromachined Capacitive Transducer Arrays for Medical Ultrasound Imaging," by X.C. Jin, F. L. Degertekin, S.Calmes X. J. Zhang, I Ladabaum, B. T. Khuri–Yakub (Stanford)(1998 IEEE Conference in Dendai).

"Novel Silicon Nitride Micromachined Wide Bandwidth Ultrasonic Transducer," by R. A. Noble, R. J. Robertson, D. R. Billson, D. A. Hutchins (University of Warwick) (1998 IEEE Conference in Sendai).

"Surface Micromachined Capacitive Ultrasonic Transducer," by Igal Ladabaum, Xuecheng Jin, Hyongsok T. Soh, Abdullah Atalar, Butrus T. Khuri–Yakub (IEEE Trans. Ultra. Ferro. Freq. Ctl vol. 45, No. 3, May 1998).

U.S. Market Overview, by Roger Grace, Roger Grace Associates, Commericialization of MEMS, Kona, Hawaii, Oct. 7, 1996, J:/MEMS/Hawaii/cs1 ™1996 Roger Grace Associates, obtained at internet address *http://www.rgraceassoc.comcom mems.html*, pp. 1–9, Dec. 3, 1998.

"Electrostatically actuated micromechanical switches using surface micromachining ", Prof. Pau Zavrack, Ph.D., obtained at internet address *http://www.ece.neu.edu/edsnu/zavracky/mfl/programs/relay/relay.html*, pp. 1–8, Dec. 31, 1998.

\* cited by examiner

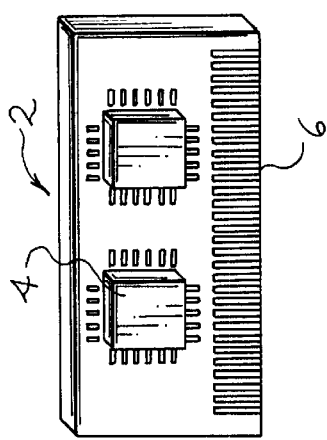
Fig. 2A
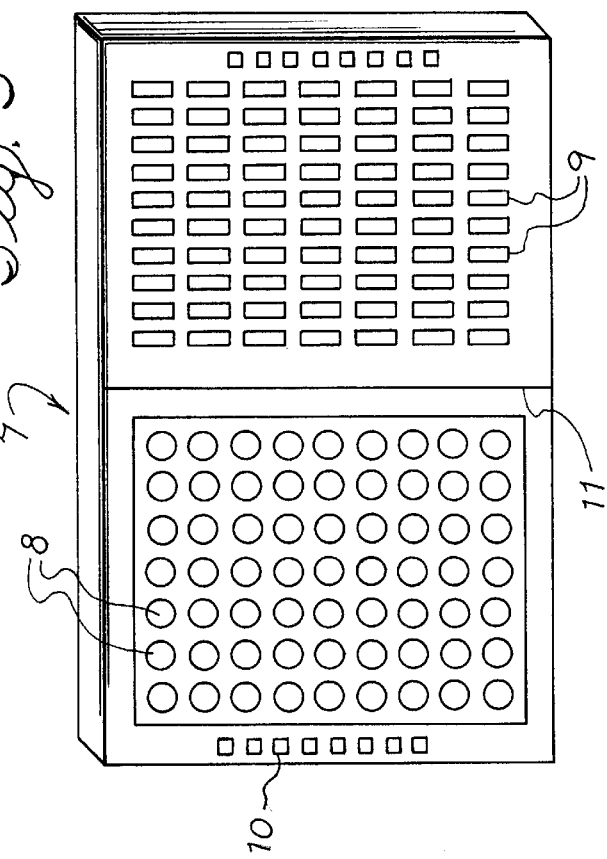
Fig. 2B
Fig. 3
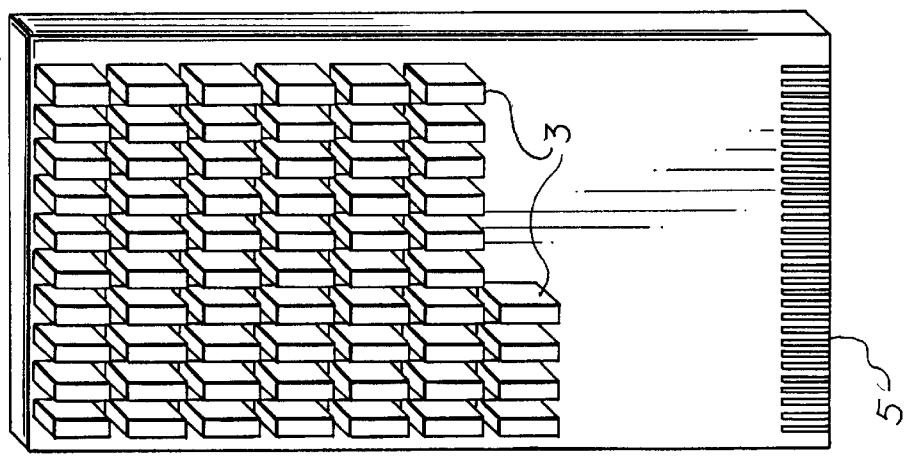

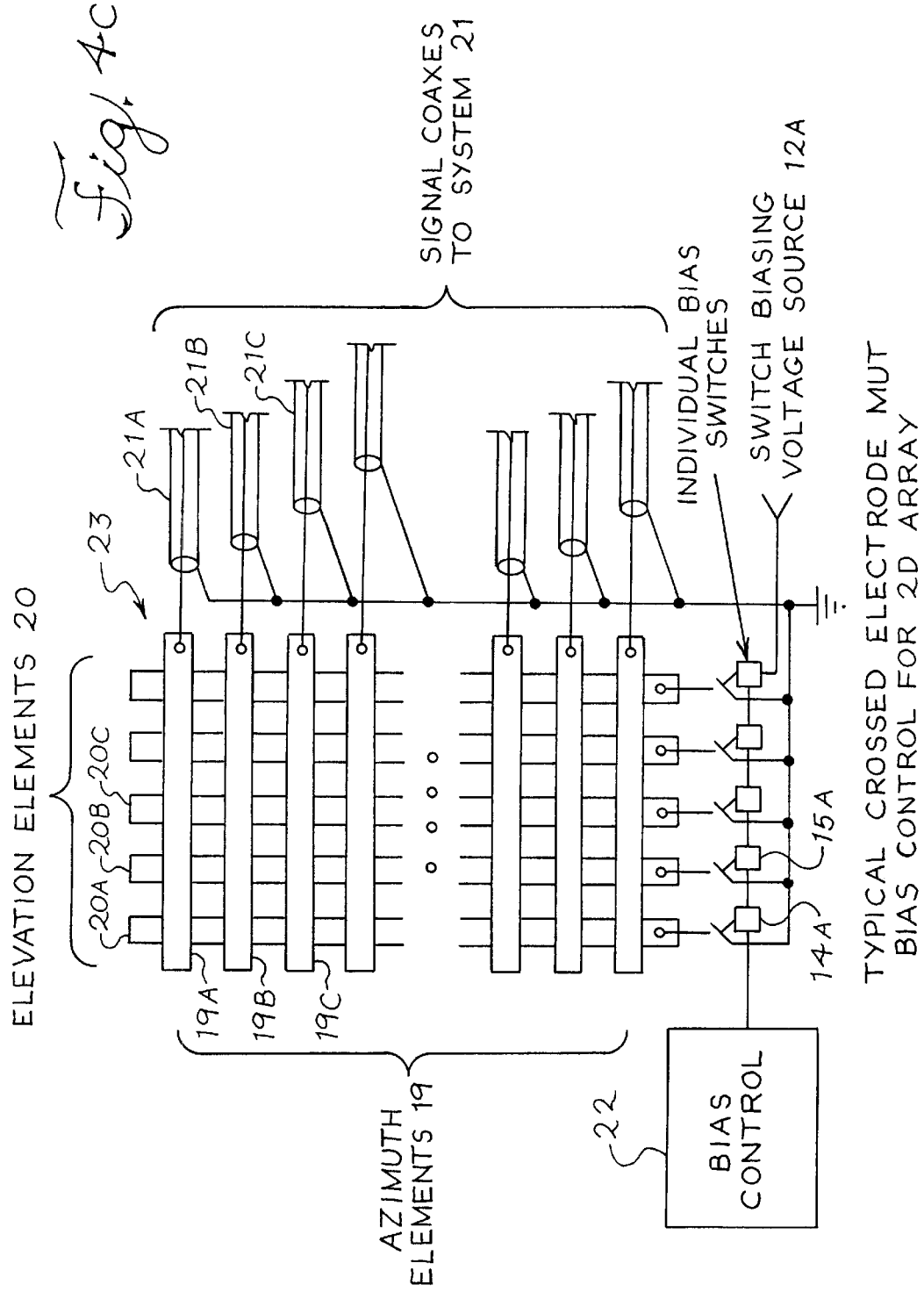

| 1 | 1 | 1 | 1 | 1 | 1 | 1 |
|---|---|---|---|---|---|---|
| 1 | 2 | 2 | 2 | 2 | 2 | 1 |
| 1 | 2 | 3 | 3 | 3 | 2 | 1 |
| 1 | 2 | 3 | 4 | 3 | 2 | 1 |
| 1 | 2 | 3 | 3 | 3 | 2 | 1 |
| 1 | 2 | 2 | 2 | 2 | 2 | 1 |
| 1 | 1 | 1 | 1 | 1 | 1 | 1 |

A 2D 49 ELEMENT APERTURE

4- HIGHEST FREQUENCY ELEMENT

1- LOWEST FREQUENCY ELEMENT

Fig. 5

DIAGNOSTIC MEDICAL ULTRASOUND SYSTEMS AND TRANSDUCERS UTILIZING MICRO-MECHANICAL COMPONENTS

REFERENCE TO EARLIER FILED APPLICATION

This application claims the benefit of the filing date pursuant to 35 U.S.C. §119(e) of Provisional Application Ser. No. 60/109,122 filed Nov. 19, 1998, the disclosure of which is hereby incorporated by reference.

BACKGROUND

Medical ultrasound imaging and therapeutic systems are rapidly becoming increasingly complex both in terms of their hardware and software. While the resulting increased diagnostic capability and value of such systems are extremely attractive to end-users, system manufacturers must assure that the increased complexity does not result in excessive cost, size, weight, or power requirements. Minimizing these physical characteristics while providing ever increasing capabilities and value has increased the manufacturers' needs for the latest in integrated circuit logic and memory devices, as well as for the latest in data-storage devices and compact efficient power supplies. In addition, these same requirements are also increasing the need for the latest in discrete electro-mechanical devices such as discrete switches and relays. Some ultrasound systems contain literally hundreds of such components, particularly in the case of newer systems having as many as 512 channels. Unfortunately, the improvement-rate for these latter discrete electro-mechanical components in terms of their integration, size, cost, efficiency, or reliability has not been as large as the improvement rate for the former above-mentioned components.

In addition, there are numerous performance reasons why today's discrete electro-mechanical devices are becoming unsatisfactory in ultrasound equipment design. Some of these reasons include high on-impedance, low off-impedance, stray capacitance, high insertion losses, high power consumption and poor power-switching capacity.

While electrical switching can be accomplished using electronic devices such as field effect transistors and thyristors, electro-mechanical contactors are preferable in certain applications. One disadvantage of electronic switches results from leakage currents that cause finite current flow in the "OFF" position. On the other hand, electro-mechanical switches have a visible open position; no current flows in the "OFF" position. The isolation in mechanical relays is determined by the contact gap, and this distance can be adjusted to suit the isolation needs of a variety of applications.

Also, in the proximity of high current systems, electronic devices are considerably sensitive to capacitive coupling and electrostatic discharge. Electro-mechanical relays exhibit good electro-magnetic compatibility, generally being insensitive to such effects.

Furthermore, today's discrete electro-mechanical devices are also physically inadequate. Ultrasound transducers increasingly need greater multiplexing capability wherein one may have many more piezoelements in the transducer than wires in the transducer cable. The current difficulty associated with such multiplexing (switching of electrical signals from a greater number of piezoelements among a lesser number of connecting wires) is that today's discrete electro-mechanical devices cannot easily be integrated in large numbers on a single IC chip. Therefore, they consume a lot of space, cost, power and weight and are avoided in large numbers, especially when the need is in the transducer or transducer connector itself.

Finally, another disadvantage of electronic switches is in the area of safety. Protective relays should in any situation which occurs, be in a position to switch off and isolate the faulty circuit. Electronic components cannot fulfill this requirement because in case of electrical breakdown or thermal overload, they generally conduct current in both directions, and are no longer able to interrupt. Thus, mechanical relays, instead of semiconductor switches, must be used for functions meant for safety.

Accordingly, there is a need for an ultrasound system for medical imaging or therapy incorporating micro-mechanical devices which retains the benefits of discrete electro-mechanical devices and provides the additional benefits of reduced size, reduced cost, improved signal integrity, reduced power consumption and higher voltage pulsing capability.

SUMMARY

By way of introduction, the preferred embodiments described below relate to an ultrasound system having the advantages of reduced size, reduced cost, improved signal integrity, reduced power consumption and higher-voltage pulsing capability. More particularly, the presently preferred embodiments relate to an improved ultrasound system incorporating micro-mechanical devices to replace "macroscopic" electro-mechanical devices in existing ultrasound designs. The presently preferred embodiments also relate to an ultrasound system which incorporates micro-mechanical devices to provide new functionality where existing electro-mechanical devices were inadequate. Given the ever-increasing bandwidth requirements of ultrasound systems coupled with their need for reduced size and cost, the potential has been recognized for micro-mechanical components to solve size, cost and power problems and allow for superior power-handling and gain the resulting superior system performance.

The preferred embodiments described below apply the new technology of micro-mechanical devices to solve the lag in the rate of improvement of electro-mechanical devices. With these preferred embodiments, for example, one may miniaturize entire switching circuit boards in existing ultrasound systems and transducers by instead employing IC-sized micro-arrays of relays and switches. This can result in drastic size, cost and power reductions as well as in several system and transducer performance-enhancements to be described herein.

It is expected that ultrasound systems and transducers, whether of handheld miniaturized portable-design or of more conventional semi-portable console-design, will benefit significantly.

BRIEF DESCRIPTION OF THE DRAWINGS

FIG. 2A is a switching board of a preferred embodiment that can be used with an ultrasound system.

FIG. 2B is a replacement switching board of a preferred embodiment utilizing micro-mechanical switches or relays.

FIG. 3 is a substrate of a preferred embodiment incorporating both an ultrasound array and a micro-mechanical switching array in close proximity.

FIG. 4C depicts schematically a crossed electrode MUT transducer of a preferred embodiment wherein the voltage bias applied to various elevation subapertures may be switched using micro-mechanical micro-relays or micro-switches.

FIG. 5 depicts a 49 element two-dimensional transducer array of a preferred embodiment wherein each element is individually switchable using a micro-mechanical switch or relay. Central elements are biased to have higher frequencies than edge elements.

DETAILED DESCRIPTION OF THE PRESENTLY PREFERRED EMBODIMENTS

Overview

Figure 1A:
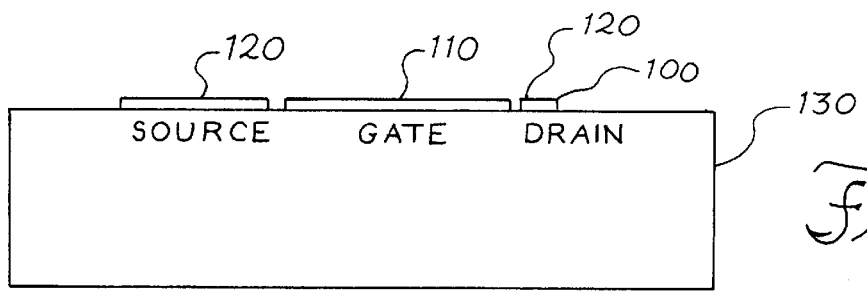
FIG. 1A shows the first metal layer step of an exemplary fabrication process for an exemplary micro-mechanical switch for use in the preferred embodiments.

The preferred embodiments relate to using micro-mechanical devices in ultrasound systems to overcome the problems of increasing size, cost and power handling that are occurring as systems designers attempt to add more value and more functionality to such systems. Specifically, the preferred embodiments relate to the use of micro-mechanical devices coupled with individual acoustic elements, transducers, transducer cables, connectors and other components of ultrasound systems. Herein, the phrase "coupled with" is defined to mean directly coupled with or indirectly coupled with through one or more intermediate components. Micro-mechanical components are used to solve multiplexing issues created by high channel count requirements (wherein the ultrasound system is capable of sending and receiving to a high number of acoustic elements, 512 or greater), to provide higher power handling capabilities and to provide for smaller transducers with new capabilities.

To address the issues of integration, size, cost, efficiency and reliability of discrete electro-mechanical devices, the field of micro-mechanics has developed. Micro-mechanics essentially involves making microscopic electro-mechanical devices of various sorts utilizing, at least in part, equipment and processes normally used to make integrated circuits on silicon, semiconductor or other dielectric wafers. Certainly the best known example of such micro-devices are the millions of silicon-based accelerometer/switches made each year for automobile airbag passenger-restraint systems. Therein, that micro-device senses de-acceleration caused by a collision and deploys the airbag(s) by electrically activating a bag-inflation triggering charge.

A micro-mechanical component or device (also known as a micro electro mechanical system ("MEMS") device) is defined as an electro-mechanical device where at least one mechanical or movable element of the component or device is manufactured (or "micro-machined"-see below) utilizing semiconductor-style processing. Such processing includes thin film deposition, patterning and etching techniques. Deposition techniques include both the physical deposition of material on a substrate and growth of a material on a substrate as are known in the art. Thin films created by such deposition techniques are generally on the order of 25 microns or less in thickness and typically 10 microns or less. Substrate materials can include semiconductor, ceramic or glass and can take the form of a wafer or other standardized form factor. Patterning techniques include lithographic patterning, printing or other form of pattern transfer, including mechanical pattern transfer, as are known in the art. Etching techniques include both chemical "wet" etching, plasma "dry" etching and laser etching as are known in the art. The term "micro-machining" is often used to refer to these semiconductor style processes utilized to fabricate micro-mechanical devices. Further, micro-machining includes both "bulk" micro-machining and "surface" micro-machining. Bulk micro-machining is the process of fabricating mechanical structures by etching the bulk of a substrate. Surface micro-machining is the process of fabricating mechanical structures on the surface of a substrate by deposition, patterning and etching layers of different materials and using other semiconductor style processes.

Figure 1B:
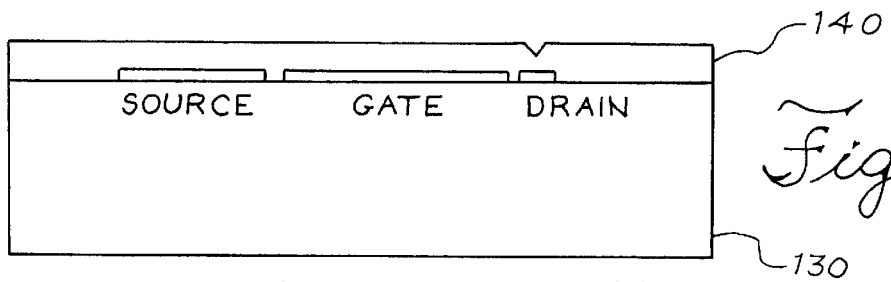
FIG. 1B shows the sacrificial layer step of an exemplary fabrication process for an exemplary micro-mechanical switch for use in the preferred embodiments.
Figure 1C:
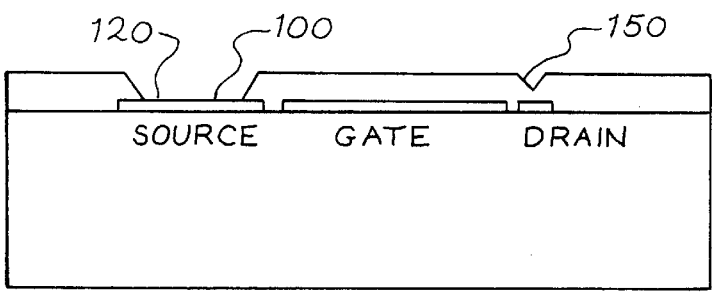
FIG. 1C shows the sacrificial layer etching step of an exemplary fabrication process for an exemplary micro-mechanical switch for use in the preferred embodiments.
Figure 1D:
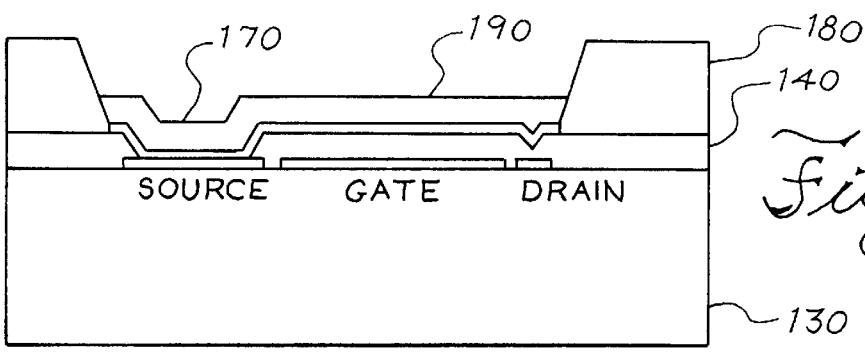
FIG. 1D shows the beam masking step of an exemplary fabrication process for an exemplary micro-mechanical switch for use in the preferred embodiments.
Figure 1E:
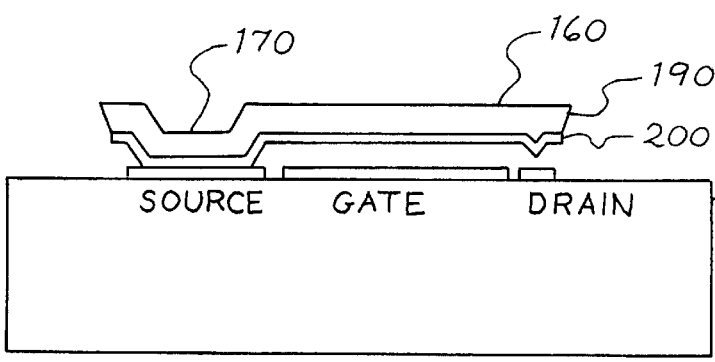
FIG. 1E shows the final etching step of an exemplary fabrication process for an exemplary micro-mechanical switch for use in the preferred embodiments.

An exemplary fabrication sequence for making a micro-mechanical switch 90 is shown in FIGS. 1A–1E. The fabrication sequence begins with the deposition and patterning of the first metal layer 100 (chrome-gold) to define the gate 110 and contact electrodes 120 on the glass substrate 130 (see FIG. 1A). A sacrificial metal layer 140 (copper) approximately 2 microns thick is then deposited (FIG. 1B). This is patterned in 2 steps. In the first step, the sacrificial layer is partially etched to define the contact tips 150 for the beam 160 (FIG. 1B). In the second etch step, the sacrificial layer 140 is etched all the way down to the source contact 100 metal to define the beam supports 170 (FIG. 1C). Subsequently, photo-resist 180 is spun on top of the sacrificial layer 140 and patterned to define the mask for the beam structure 160. The beam 160 consists of a 2 micron thick layer of nickel 190 on top of a 200 nm thick layer of gold 200. Both these layers 190, 200 can be formed either by electroplating or by electroless plating (FIG. 1D). The gold layer 200 serves as the contact material with the gold contact pads when the switch closes. Finally, the sacrificial layer 140 is removed by a suitable wet etching process to release the free-standing beam 160 (FIG. 1E).

Micro-mechanical devices can be fabricated one at a time or in large numbers on a wafer (or substrate) of silicon, glass or ceramic-taking advantage of the batch-nature of semiconductor processing. The device can incorporate moving members such as deflecting micro-cantilevers, deflecting diaphragms, etc. as are known to the micro-mechanical art. The device can also incorporate a moving gas or fluid as in a micro-fluidic or micro-pneumatic device. The moving members of such devices can move by distortion, deformation, translation, deflection, rotation, torsion or other motion. Further, micro-mechanical devices can incorporate at least one of electrostatic, magnetic, piezoelectric, electro-magnetic, inertial, pneumatic, hydraulic or thermal micro-actuation mechanisms. Prototype micro-mechanical switches in particular have used electrostatic, magnetic, electro-magnetic, thermal and inertial micro-actuation means. The possible micro-actuation mechanisms for switches and relays are therefor several and well known in the art, and therefore are not critical to the invention. The fact that such devices are employed in ultrasound applications in micro-mechanical form resulting in performance, cost, packaging and reliability advantages is the focus herein. Other micro-mechanical devices such as chemical sensors may have no physical/mechanical actuation means, and provide only a passive readout. Typically, micro-mechanical devices are provided to customers in the form of packaged chips. The chip-packages are typically IC-Chip packages (ceramic, plastic, metal etc) and each contains at least one and sometimes numerous devices.

Of particular interest in the design of ultrasound imaging systems is the promise of arrays of micro-mechanical switches or relays with which one might virtually eliminate existing large printed circuit boards currently populated with discrete versions of such current-art switches and relays. Using micro-arrayed micro-relays or micro-switches made using micro-mechanical techniques one may place any desired number of such components in an extremely compact device allowing new design freedom.

It is important to note that although we primarily focus herein on micro-mechanical switches and relays as the immediate preferred ultrasound-imaging embodiments, it is anticipated there are additional micro-mechanical applications in ultrasound, both electrical and mechanical, which this invention now makes recognizable. These include, for example, other components such as micromechanical inductors, micro-mechanical optical-fiber switches, micro-mechanical phase-shifters, micro-mechanical connectors (electrical, optical, hydraulic and pneumatic), micro-mechanical fuses and circuit-breakers, as well as micro-mechanical valves and micro-mechanical biometric user-identification devices such as the recently announced fingerprint pressure-sensing chips.

There is ongoing research in the field of micro-mechanics and current market projections for the micro-mechanical market particularly show the total micro-relay market to currently be in evolution, with full market-commercialization expected in the year 2006. There is ongoing work in the area of electrostatically actuated micro-mechanical switches and relays resulting in likely fabrication processes and materials useful for making arrays of micro-mechanical switches which we see as applicable to ultrasound systems.

There is further work being done on micro-relays and on nickel micro-relays. There are references which describe work relating to micro-fuses, or more correctly micro-circuitbreakers for satellite applications, and references which describe work on contactless capacitive switch arrays in micro-mechanical form. Additional references describe the attractiveness of micro-mechanical-switch based phase-shifters, particularly showing that such devices have been measured to have only 0.2 dB insertion loss at 10 Ghz. It is noted that applications to ultrasound for achieving beam-steering phase-shifts and signal mixing and manipulation are also very attractive.

In particular, the micro-mechanical switch is a much more natural device for phase shifting. In essence, this is a miniaturized version of the venerable toggle switch so familiar in electronic components. In the spatial-power combining area, micro-mechanical switches can also be beneficial as phase shifters, but in a different implementation than the planar case. Since planar arrays operate on the entire wave front, the micro-mechanical phase shifters can be added to each cell to introduce the proper amount of phase shift required to steer the beam. In many ways, this function is similar to that carried out in optics by a prism with the additional benefit that the difference between entry and exit angles of the beam is under electronic control.

Further references provide overviews of micro-mechanical devices and describe work on micro-machined silicon variable inductors and latching accelerometers. It is noted that such inductors are extremely attractive to ultrasound because of their low parasitics, excellent open-state isolation and their described programmability.

Additionally, the following two references, which are hereby incorporated by reference, relate to micro-mechanical switches and/or relays: (1) "Fully integrated magnetically actuated micro-machined relays" by W. Taylor et al appearing in the Journal of Microelectromechanical Systems, Jun. 1, 1998, v7 n2, p181; and (2) "Characteristics of micro-mechanical electrostatic switch for active matrix displays" by T. Nishio et al appearing in IEICE Transactions on Electronics, Sep. 1, 1995, v78, n9, p1292.

While micro-mechanical devices offer many advantages, some of the main advantages are simply power handling, size and the ability to pack a lot of devices in a small area. With the ever increasing bandwidth needs of today's ultrasound systems, the ability to densely pack components capable of high power pulse manipulation is highly advantageous so as not to wind up with a system that is too unwieldy in both size and power use.

First Preferred Embodiment

One of the main areas where the consequences of increasing channel count and bandwidth are apparent is in ultrasound system switching boards. Switching boards inside ultrasound systems or consoles are frequently utilized to route system signals to and/or from a number of transducer connector receptacles mounted on the system's exterior. Each of these exterior system connectors may have anywhere from 64 to 512 or more contacts and there may be as many as 4–6 such transducer connectors. The pluggable imaging transducers, in the case of their not being multiplexed, have a number of piezoelements in their acoustic arrays which corresponds roughly to the number of pins in their respective connectors. Ultrasound imaging transducers increasingly have a very large number of piezoelements (e.g. 200–500 or more) and therefor may also require switches located in the transducer itself such that the huge number of piezoelements may share (i.e. multiplex) a smaller and more reasonable number of cable wires. In other cases, an array of switches may be provided in the transducer connector itself (at the system end of the transducer cable) in order to tie together (share) a first number of transducer piezoelements with a second differing number of available system channels. This approach can minimize transducer weight and power consumption because the user does not hold the switches in his/her hand while holding the probe. Further, by allowing for higher pulsing voltages addressed to an ever larger number of acoustic elements, currently weak harmonic acoustic signals and bandwidth can also be enhanced.

FIG. 2A shows a schematic (not to scale) of a prior-art system switching board 1 as described above. The board 1 is populated with a large number of prior-art relays 3, perhaps 128 or more, arranged on at least one of its two major surfaces. The board 1 is shown as having conventional edge-card connector contacts 5. In one particular case a board is currently used having 128 SPDT (single pole double throw) relays 3. Such relays 3 can be purchased from vendors such as Omron, Hamlin, CP Clare and Cotto. Such prior-art relays 3 are each approximately 0.75 inch long by 0.25 inch wide by 0.25 inch tall thus their individual board footprint is approximately 0.75 by 0.25 inches. In addition one should preferably have about 0.25 inches of spacing between any two such relays to minimize electrical crosstalk. It can thus easily be seen that the switching board 1 may be quite large, with its maximum dimension over a foot or 12 inches in size or more. The very best technology currently available from SuperTex, Inc. (not shown in figure) allows for up to 16 such functionally similar switches 3 to be co-integrated in a single housing measuring about 0.46 by 0.46 inches in footprint. While using such switches yields a smaller circuit board, they still fail to satisfy the increasing need for such components.

FIG. 2B shows the first major embodiment of the invention. Therein is shown a much smaller (relative to board 1) board 2 having two micro-mechanical micro-relay chips 4 each approximately 0.5–1.0 inches square as-packaged and surface-mounted on the board 2. Each of these micro-mechanical relay chips 4 very easily contains 64 micro-relays each; thus this board 2 is the operational equivalent of the prior art board 1 yet is 5–10 times or more smaller, consumes far less power, is far less expensive and is capable of switching higher voltages, especially if the numerous micro-relays are ganged. Board 2 is also shown as having edge-card connections 6. Using the preferred embodiment described herein, the board 2 may have dimensions in the range of 2 or less inches tall by 6 or less inches wide. At the same time the electrical performance benefits mentioned earlier are gained over the conventional relay approach of the prior art board 1 and its devices 3. Research being done on micro-relays shows that as many as 20,000 individual relays might be integrated on a single chip-but for practical purposes, taking yield and the use of ganged relays used in parallel to achieve higher current handling into account, the number is more like 1000 relays per chip. Thus it can be seen that the 64 relays per chip example, even if each of the 64 is a parallel-ganged group of 8, is easily done using micro-mechanical technology.

Note that micro-relays are distinguished from micro-switches by the relationship between the actuator and the contacting functions. In a relay, the actuator and switching functions are separated and electrically isolated requiring a minimum of four terminals.

A major variation on the first embodiment is to provide miniaturized micro-relay switching in the transducer itself (or in the transducer connector at the system-end of the transducer cable) for purposes of multiplexing a greater number of acoustic elements (or system channels) among a lesser number of transducer cable-wires. An existing state of the art transducer has a 256 wire cable and a 512 element acoustic array. At the current time this transducer requires two multilayer double-sided switching boards each about 2 by 3 inches in size to be packaged inside of it. These boards support 44 SuperTex, Inc. switching chips, each such chip having 6 switches and having a 0.46 by 0.46 footprint. The same switching capability can be provided using one board about one-third the size with only a single-side mounting of one micro-relay-array chip. This represents a huge cost, power and performance advantage.

Second Preferred Embodiment

Moving now to the second major embodiment of the invention FIG. 3 shows a co-integrated ultrasound array and micro-relay (or micro-switch) array. A transducer substrate 7 is shown which may be a silicon chip, silicon on glass, glass or ceramic substrate. An array of acoustic elements 8 is shown on the left side. An array of micro-relays 9 is shown on the right side. Sets of wirebond pads 10 are shown for purposes of connection to the outside world. By co-integrating micro-relays or micro-switches 9 with the acoustic array elements 8, on-board local switching of signals to and from the individual acoustic array elements 8 can be performed. A typical ultrasound application would have more piezoelements 8 than wires in the cable (cable wires attachable, for example, at bondpads 10) running to and from the transducer 7. The local micro-relays 9 would allow multiplexing or switching of the acoustic elements 8 among the lesser number of wires (wires would connect to bondpads 10). This is called multiplexing.

As an example, for a catheter-based transducer, one might have 8 wires in the cable (for reasons of low cost, small cross-section and flexibility) and have 256 acoustic elements 8 in the acoustic array being switched among the 8 wires (not shown) by 256 micro-relays 9. Obviously one might employ a variety of laparascopes or other low-cost tubular medical scopes for mounting such a transducer having integrated switching. Such co-integration would allow for such a reduced cost as to make a disposable version of such a catheter-based transducer possible.

It is important to note several details about device 7. The first is that the acoustic elements 8 may be of any variety including thin-film elements (e.g. zinc-oxide or pzt) or electrostatic capacitive micro-mechanical elements. The second is that the array of elements 8 may take on any array geometry such as linear or two dimensional arrays. The third is that the micro-relays (or micro-switches) 9 may be on the same side (shown) or on the opposite face of the chip (not shown) and connected via wrap-around edge or through-via connections. They may also be intermixed within the acoustic element array. The fourth is that the means of external interconnection is not important and although wirebond pads 10 are indicated one may just as well utilize flip-chip or tape-automated bonding means. The fifth and last important point regarding FIG. 3 is to note the phantom line 11 across the substrate 7. This indicates that a seam or joint may be present here and rather than having one monolithic substrate one actually may have two or more closely arranged substrates serving the equivalent purpose as a single monolithic substrate 7. In that case seam 11 would represent the interface between two or more such independent substrates 7 and 7' (not shown) arranged or abutted close together. One may also choose to mount separate substrates such as 7 and 7' on a third substrate (not shown) such that a conventional hybrid circuit is created wherein 7 and 7' are at least two components mounted thereon. In this case the mother substrate would have the interconnects necessary to route signals etc between 7 and 7' and components 7 and 7' might be mounted on the mother substrate using BGA (ball grid array) interconnection means.

Obviously there are many interconnects in FIG. 3 (not shown) that need to run between the relays 9 and the acoustic elements 8 and pads 10. By utilizing two or more separate substrates 7 having at least one seam 11 it is necessary to form connections across that seam. It is important to note that the preferred embodiments also expressly include the case wherein two substrates are used, a 7 and a 7' (not shown). One of these is bonded directly to the other in a face to face (or edge to edge) manner using ball-grid array (BGA) interconnection techniques thus forming all of these needed interconnections at one time and providing a single (albeit laminated) chip serving the acoustic and switching functions.

Device 7 may also, as desired, be joined or abutted to other useful acoustic components (not shown) such as matching layers, attenuative backers, isolation windows or acoustic lenses.

It has been found that the cost reductions made possible with the approaches described for FIG. 3 allow for inexpensive disposable high-quality arrays to be made in huge numbers in wafer-form using automated equipment.

Note that arrayed micro-machined devices such as 4 and 9 may be any useful component, whether passive or active, wherein an acoustic array is being supported by one or more such micro-mechanically miniaturized devices and substantial space, power and cost is thereby being saved or signal integrity is improved. An excellent example of a component different than a switch or relay would be wherein each device 9 (or 4) is a micro-mechanical inductor or array of micro-mechanical inductors used for purposes of impedance matching the transducer to the system. In a manner similar to prior-art switches, prior-art inductors also consume huge amounts board space. Finally, device array 4 or device 7 may also attractively incorporate memory means used for storing transducer identification, transducer history, transducer beamforming microcode, transducer calibration information or the like.

Note also that conventional prior art relays typically only handle up to about plus and minus (+/−)100 volt pulses whereas micro-relays, particularly when used in ganged fashion, have been shown to switch up to plus and minus (+/−)300 volt pulses. The additional voltage capability provides a stronger acoustic transmit pulse thereby also a stronger returned acoustic signal (keeping within FDA acoustic power-limits of course). The stronger transmit pulsing ability is very useful to enhance the harmonic returned signals such as are looked at in harmonic imaging modes such as Acuson's Native Tissue Harmonic Imaging™ modality. In such harmonic operating modes the returned harmonic signal can be relatively weak (relative to the transmitted fundamental frequency) and anything that can increase the returned harmonic signal's amplitude is highly attractive. The higher-voltage pulsing ability is also very useful when constructing sparsely populated two dimensional acoustic arrays (which are capable of volumetric 3D imaging) wherein one needs to maintain a good signal despite the leaving out of a good chunk of the elements (left out mainly for yield and cost reasons).

Device 7 may utilize multilayer or laminated (interlayer electroded) piezoelements 8 as is known for improving impedance matching of the transducer to the system driving electronics. Elements 8 may also be arranged in multiple apertures (strips for example) such that said apertures can separately be switched on and off for purposes of narrowing the acoustic beam in the nearfield as has recently been practiced in the art. Elements 8, or groups thereof, may likewise be arranged to have differing acoustic performance or different electroacoustic or material properties. In this manner one may again manipulate the overall acoustic beam's spectral behavior by switching among such differing elements for purposes such as increasing bandwidth, creating notches in the spectrum, achieving a real apodization or switching among layers of a multilayer element(s) 8.

Third Preferred Embodiment

The next major preferred embodiment refers to a particular type of transducer acoustic element known as a MUT or a "micro-mechanical ultrasound transducer". In the preferred embodiment a cMUT or capacitive (electrostatic) MUT is utilized. These are essentially electrically driveable vibrating micro-diaphragms or membranes made using micro-mechanical techniques wherein on each side of the vibrating diaphragm (membrane)/chamber is a capacitor electrode and the lateral (largest) dimensions of the diaphragm(s)/membrane(s) may be as small as in the micron range. Examples of such devices and processes necessary for their fabrication are known in the art. Additionally the following reference papers, all of which are incorporated by reference, discuss cMUTS in some detail:

"Micromachined Capacitive Transducer Arrays for Medical Ultrasound Imaging" X. C. Jin, F. L. Degertekin, S. Calmes X. J. Zhang, I Ladabaum, B. T. Khuri-Yakub (Stanford)(1998 IEEE Conference in Sendai);

"Novel Silicon Nitride Micromachined Wide Bandwidth Ultrasonic Transducers" R. A. Noble, R. J. Robertson, D. R. Billlson, D. A. Hutchins (University of Warwick) (1998 IEEE Conference in Sendai); and "Surface Micromachined Capacitive Ultrasonic Transducers" Igal Ladabaum, Xuecheng Jin, Hyongsok T. Soh, Abdullah Atalar, Butrus T. Khuri-Yakub (IEEE Trans. Ultra. Ferro. Freq. Ctl Vol 45, No. 3, May 1998).

Figure 4A:
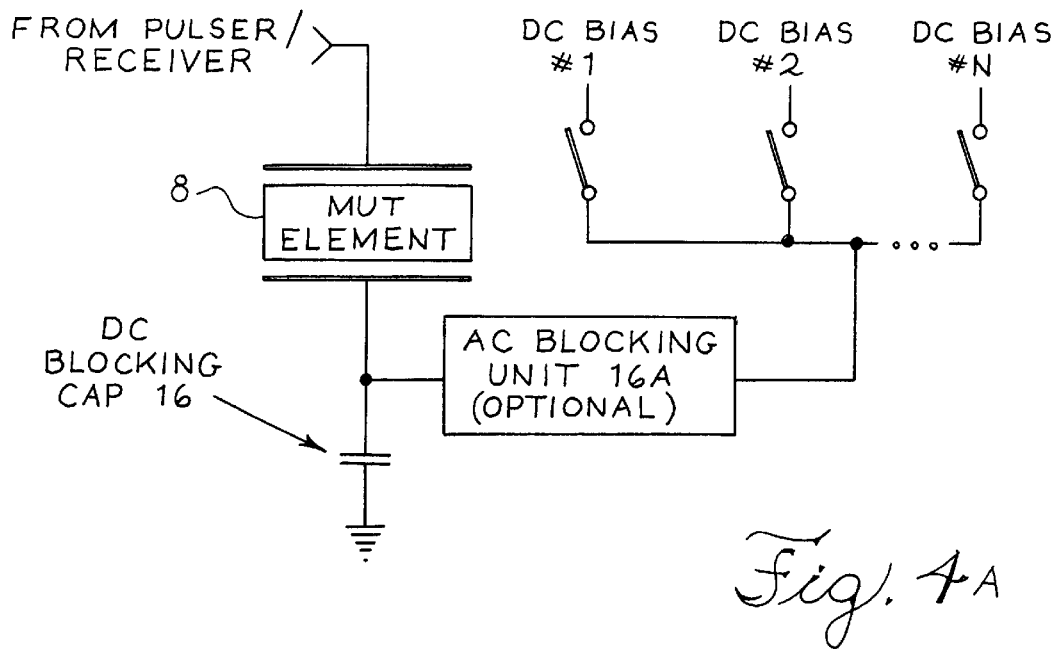
FIG. 4A depicts schematically how a switchable voltage bias may adjust the center frequency of a capacitive micro-mechanical ultrasound transducer (cMUT) of a preferred embodiment.

Moving now to FIG. 4A, a capacitive micro-mechanical acoustic element's (cMUT's) center frequency is known to be controlled by a DC bias voltage applied across it (see above Ladabaum reference for example). This is essentially because a DC bias stresses the membrane in increased tension which allows a higher restoring force during vibration. FIG. 4A shows schematically one such element 8 which, in this example, is a micro-mechanical capacitive acoustic element or cMUT. On the right hand side of FIG. 4A can be seen several voltage inputs 12,13 . . . N which are each biasing source-means capable of providing a particular DC bias voltage to element 8. Thus by micro-switching via the use of micro-relays 14, 15 . . . one may apply a voltage bias of desired value to cMUT 8, thus setting its center frequency to a desired value. In a very desirable implementation of this invention, it is arranged for a first bias voltage 12 to cause element 8 to operate at its center frequency in transmit. A DC blocking capacitor 16 is also provided as is an optional AC blocking unit 16a. Upon acoustic reception, after a time delay, the second bias voltage 13 (or both added together), is instead applied to element 8 causing element 8 to have a characteristic reception acoustic operating spectrum in the neighborhood of a desired (usually higher) harmonic receive-frequency. As an example the cMUT center transmit-frequency might be 3.5 MHz using bias 12 and the higher cMUT first-harmonic frequency might be 7.0 MHz using bias 13. Such frequency switching for harmonic imaging is known to the art. It will be appreciated that the transmit pulse voltage to the cMUT is applied in the presence of the first bias and acoustic receive is done using the second bias. It is apparent that one may alternatively have separate transmit and receive elements 8—ie dedicated elements. Further, there is no need to restrict the number of bias voltages to just two.

Figure 4B:
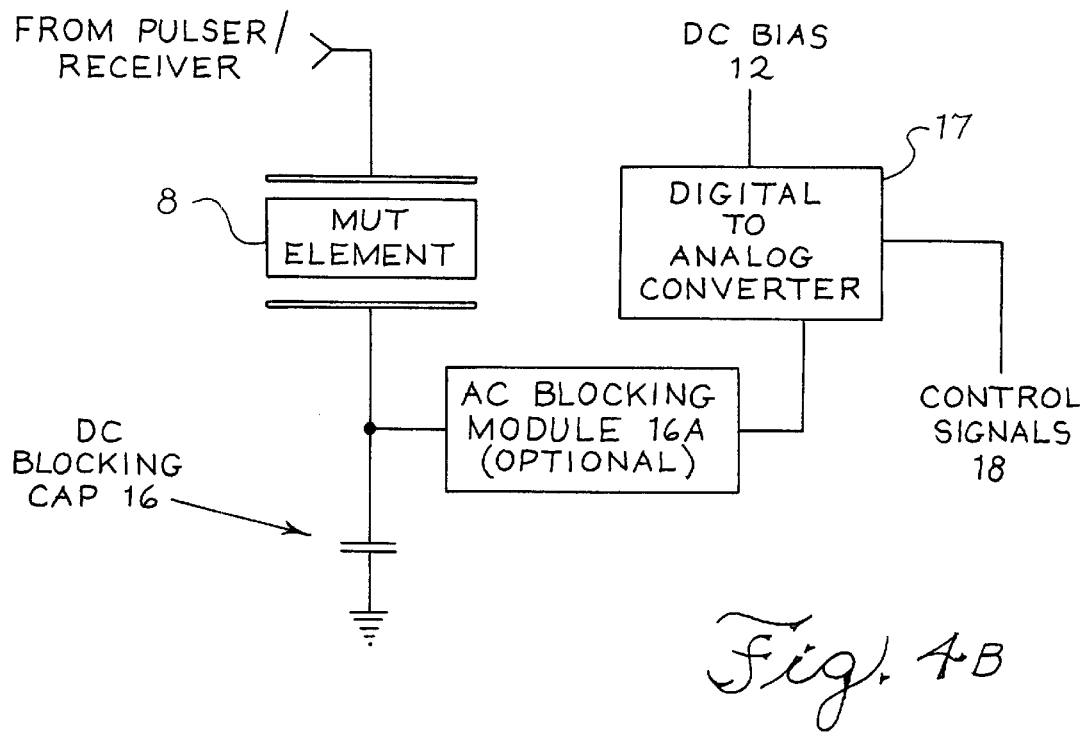
FIG. 4B depicts schematically a particularly preferred embodiment of the biasing of FIG. 4A utilizing a digital/analog (DAC) converter comprising micro-mechanical switches and resistors to control voltage bias applied to the cMUT(s) using a single source bias.

FIG. 4B depicts schematically a particularly preferred embodiment of the biasing of FIG. 4A wherein instead of using a discrete array of micro-mechanical switches to switch a number of fixed voltage bias sources (FIG. 4A), a digital/analog (DAC) converter comprising micro-mechanical switches and resistors is used wherein the micro-mechanical based DAC allows one to control voltage bias applied to the cMUT(s) using a single source bias.

In FIG. 4B, a cMUT is shown having a bias voltage control for varying the center frequency. However rather than providing multiple unique bias voltages which are each separately switchable (as in FIG. 4A) we instead use a single bias voltage source 12 routed to a DAC 17. Also routed into the DAC 17 are control signals 18. By sending appropriate digital control signals 18 to the DAC 17 one controls the voltage bias being applied to cMUT 8 to be some portion of voltage 12. As an example, the bias 12 might be 200 volts and the DAC allows provision of 16 or 32 lesser reduced voltages. Furthermore, the DAC 17 itself may be constructed from micro-relays or micro-switches combined with resistors. The resistors may be laser-trimmed at manufacturing for extra precision during the setting of the values for each of the voltage choices. Thus from FIG. 4B we see that micro-mechanical techniques may be employed for both the acoustic element fabrication as well as fabrication of supporting electronic components.

FIG. 4C shows another application for micro-mechanical micro-relays or micro-switches. A plan view of a transducer array 23 is shown. The array 23 has orthogonal (or crossed) electrode sets. One electrode set 19 (19a, 19b, 19c . . . ) addresses individual piezoelements linearly arrayed along the azimuth (top to bottom) direction. The other electrode set 20 (20a, 20b, 20c . . . ) addresses common subportions of the elevation of each piezoelement. It will be seen therein that 20a, 20b, 20c . . . are switchable to the variable bias source via micro-mechanical micro-relays or micro-switches 14a, 15a . . . The array is shown having a bias voltage source 12a and a means of bias control 22. It will be clear to those skilled in the art that with this electrode arrangement one may accomplish a variety of useful benefits. A first example is wherein the array consists of poled PZT piezomaterial and the micro-mechanical micro-relays are used simply to turn on and/or off various portions of the elevation length of all the elements thus obtaining a beneficial narrowing (or translation) of the elevation slice thickness either during transmit, receive or both-especially for near-in imaging.

A second example is wherein the array consists of electrostrictive piezomaterial such as PZN whose acoustic response is maintained not by permanent poling but instead by application of a selectable temporary bias to achieve a selectable response level. In this scheme, the biasing takes the place of the permanent poling but the piezomaterial still needs to be pulsed for transmit (with the bias applied). At any rate, using the electrostrictive material, one can thereby now control the magnitude of the acoustic response (in transmit and receive) as well as whether the element or elevation-portion of the element is on or off. Coax cables (wires or board traces) 21 (21a, 21b, 21c . . . ) are shown routed to the electrodes of the type 19a, 19b, 19c on each piezoelement.

FIG. 5 shows a square two-dimensional (2D) array consisting of a 7 by 7 array (or 49 total) of elements. The elements are labeled with the digits 1, 2, 3 or 4 as can be seen in the figure. The digits 1–4 represent four levels of center frequency as might be desired for a very broadband array. The levels can be distributed as shown with higher frequency (e.g. 4) in the center and lower frequency (e.g. 1) at the array's edges. Each cMUT acoustic element (49 total) in this array is addressable by at least one dedicated micro-relay or micro-switch and interconnect (not shown) capable of applying the desired bias level to its companion element. The benefits of frequency variation across an array are well known in the art.

In FIG. 5, in addition to or alternatively to controlling element frequency one may also, or instead, control the on/off state or the degree of electroacoustic activity (e.g. using electrostrictive piezomaterial). Thus, for example, one might pass a moving linear aperture across the face of the array for 3D imaging one plane at a time or simply weaken certain elements for apodization purposes.

It must be emphasized that 2D arrays, as shown in FIG. 5, are currently exceedingly expensive to build because one requires N squared or N×N switches. The use of micro-relays or micro-switches solves this problem both from the cost point of view as well as from the packaging and miniaturization point of view.

It is further noted that one may employ a "sparse array" design for the device of FIG. 5 (not shown) wherein only a selected portion of the elements are actually acoustically operated.

The following list summarizes attractive ultrasound applications utilizing micro-mechanical devices as show in the last two figures:

1. Element switching and aperture apodization (sensitivity control) in both single and 2D arrays on an element by element (if necessary) basis;
2. Element switching and sensitivity control in 2D arrays using a crossed electrode technique (a reduced complexity technique relative to 1.);
3. Element frequency control/tuning in both single and 2D arrays on an element by element basis allowing for "variable frequency vs. location" type apertures;
4. Element frequency control/tuning in 2D arrays using a crossed electrode technique;
5. Frequency control/tuning in single and 2D arrays in a time varying manner to better implement harmonic imaging. Low frequency transmit then rapidly switch to high frequency (or harmonic) receive;
6. Aperture translation and/or rotation of a slice image plane within a 2D array; and
7. Low cost and compact fully-switchable 2D arrays used for any purpose (3D beamforming or moving-aperture 2D and/or 3D imaging.

It is to be understood that a wide range of changes and modifications to the embodiments described above will be apparent to those skilled in the art, and are contemplated. It is therefore intended that the foregoing detailed description be regarded as illustrative rather than limiting, and that it be understood that it is the following claims, including all equivalents, that are intended to define the spirit and scope of this invention.

What is claimed is:

1. An ultrasound system for medical imaging or therapy comprising:
   at least one ultrasonic acoustic element;
   said at least one ultrasonic acoustic element comprising at least one micro-mechanical component coupled with said at least one ultrasonic acoustic element, said component comprising
      at least one movable mechanical element fabricated on a substrate utilizing at least one integrated circuit manufacturing process wherein said at least one movable mechanical element is a member selected from the group consisting of a beam, cantilever, fluid and gas.

2. The invention of claim 1, wherein said at least one movable mechanical element moves by a motion selected from the group consisting of deflection, sliding, distortion, translation, rotation, torsion and deformation.

3. The invention of claim 1, wherein said at least one integrated circuit manufacturing process comprises:
   formation of at least one thin film material on a substrate;
   formation of a pattern in said at least one thin film material; and
   etching of said at least one thin film material.

4. The invention of claim 3, wherein said formation of said at least one thin film material is by a process selected from the group consisting of deposition and growth.

5. The invention of claim 3, wherein said formation of said pattern is by a process selected from the group consisting of lithography, printing and mechanical pattern transfer.

6. The invention of claim 3, wherein said etching process is a process selected from the group consisting of wet chemical, plasma and laser etching.

7. The invention of claim 3, wherein said at least one thin film material is characterized by a thickness less than 25 microns.

8. The invention of claim 1, wherein said movable mechanical element is characterized by at least one physical dimension measuring less than 10 microns.

9. An ultrasound transducer comprising:
   at least one array of at least one ultrasonic acoustic element; and
   said at least one ultrasonic acoustic element comprising at least one micro-mechanical component coupled with said at least one ultrasonic acoustic element, said at least one micro-mechanical component comprising at least one movable mechanical element fabricated on a substrate utilizing integrated circuit manufacturing processes wherein said at least one movable mechanical element is a member selected from the group consisting a beam, cantiliever, fluid and gas.

10. The invention of claim 9, wherein said at least one movable mechanical element moves by a motion selected from the group consisting deflection, sliding, distortion, translation, rotation, torsion and deformation.

11. The invention of claim 9, wherein said integrated circuit manufacturing processes comprise substrate deposition and etching processes.

12. The invention of claim 9, wherein said movable mechanical element is characterized by at least one physical dimension measuring less than 10 microns.

13. The invention of claim 9, wherein said at least one micro-mechanical component comprises a device selected from the group consisting of a relay, switch, inductor, circuit-breaker and fuse.

14. The invention of claim 9 wherein said ultrasound transducer comprises a catheter mounted transducer.

15. The invention of claim 14, wherein said catheter mounted transducer is disposable.

16. The invention of claim 9, wherein said ultrasound transducer comprises a scope mounted transducer.

17. The invention of claim 16, wherein said transducer is disposable.

18. The invention of claim 9, wherein said at least one acoustic element of said transducer is fabricated utilizing micro-machining means.

19. The invention of claim 9, wherein said ultrasound transducer is provided in a hand held form factor.

20. The invention of claim 9, wherein said at least one micro-mechanical component switches 150 volts or greater.

21. The invention of claim 20, wherein said at least one micro-mechanical component switches bipolar voltage.

22. The invention of claim 20, wherein said at least one micro-mechanical component switches unipolar voltage.

23. The invention of claim 9, wherein said micro-mechanical component is operative to enable return of a greater harmonic acoustic signal.

24. The invention of claim 9, wherein said ultrasound transducer is a two-dimensional ultrasound transducer array comprising N×M acoustic elements.

25. The invention of claim 24, wherein said at least one micro-mechanical component is operative to control the motion of a two dimensional transmit/receive scan plane emanating from/to said two-dimensional ultrasound transducer array.

26. The invention of claim 24, wherein a sub-set of said N×M elements are utilized to provide a sparse two-dimensional ultrasound transducer array.

27. The invention of claim 9, wherein said at least one ultrasonic acoustic element is characterized by at least one electrical impedance and further wherein said at least one micro-mechanical component comprises at least one micro-mechanical inductor wherein said at least one micro-mechanical inductor is operative to better match said at least one electrical impedance of said at least one ultrasonic acoustic element to an electrical impedance characteristic of an ultrasound system.

28. The ultrasound transducer of claim 9, wherein said at least one array comprises at least 256 of said at least one ultrasonic acoustic element.

29. The ultrasound transducer of claim 9, wherein said at least one array comprises a one dimensional array.

30. An ultrasound system for medical imaging or therapy comprising:
   at least one ultrasonic acoustic element; and
   at least one micro-mechanical component coupled with said at least one ultrasonic acoustic element;
   at least one substrate comprising a first and second section;
   wherein said first section comprises said at least one micro mechanical-component and said second section comprises said at least one ultrasonic acoustic element.

31. The invention of claim 30, wherein said first and second sections are joined.

32. The invention of claim 30, wherein said first and second sections are joined via area-wise bump-array bonding.

33. The invention of claim 30, wherein said at least one acoustic element comprises a thin-film element.

34. The invention of claim 30, wherein said at least one acoustic element comprises an electrostatic capacitive micro-mechanical element.

35. The invention of claim 30, wherein said at least one substrate is located within a catheter mounted transducer.

36. The invention of claim 35, wherein said catheter mounted transducer is disposable.

37. An ultrasound transducer for medical imaging or therapy comprising:
   at least one ultrasonic acoustic element;
   at least one micro-mechanical component coupled with said at least one ultrasonic acoustic element;
   at least one substrate comprising a first and second section;
   wherein said first section comprises said at least one micro mechanical-component and said second section comprises said at least one ultrasonic acoustic element.

38. The invention of claim 37, wherein said first and second sections are joined.

39. The invention of claim 38, wherein said first and second sections are joined via area-wise bump-array bonding.

40. The invention of claim 37, wherein said at least one acoustic element comprises a thin-film element.

41. The invention of claim 37, wherein said at least one acoustic element comprises an electrostatic capacitive micro-mechanical element.

42. An ultrasound transducer comprising:
   at least one array of at least one ultrasonic acoustic element, said at least one array arranged in at least one dimension and operative to provide harmonic image information wherein a first bias is provided to said at least one acoustic element during transmit and a second bias different from said first bias is provided to said at least one acoustic element during receive;

at least one micro-mechanical component coupled with said at least one acoustic element.

43. The invention of claim 42, wherein said ultrasound transducer array operates at a first frequency in transmit and a second frequency in receive.

44. The invention of claim 42, wherein said micro-mechanical component comprises a device selected from the group consisting of a micro-relay and micro-switch.

45. The invention of claim 42, wherein said at least one micro-mechanical component is operative to selectively connect and disconnect a voltage bias source forming a digital to analog converter used to vary the voltage bias provided to said at least one acoustic element.

46. The invention of claim 42, wherein said ultrasound transducer array has a crossed electrode arrangement.

47. The invention of claim 42, wherein said ultrasound transducer array has dedicated electrodes for each of said at least one acoustic element.

48. The invention of claim 42, wherein said at least one acoustic element comprises a property of spectral frequency and further wherein the spectral frequencies of at least two acoustic elements of said ultrasound transducer array are set to different values to attain broadband acoustic behavior.

49. The invention of claim 42, wherein said ultrasound transducer array is operative to produce a harmonic image wherein said array provides a higher voltage pulse to enhance at least one harmonic signal.

50. The invention of claim 42, wherein said at least one acoustic element is a micro-mechanical ultrasound element.

51. The invention of claim 50, wherein said micro-mechanical ultrasound element is a capacitive micro-mechanical ultrasound element.

52. The invention of claim 42, wherein said at least one acoustic element comprises a property of signal phase and further wherein said signal phase property comprises the phase of the transmit signal.

53. The invention of claim 52, wherein said signal phase is controlled for the purpose selected from the group consisting the purposes of beam-steering, signal-mixing and signal-manipulation.

54. The invention of claim 42, wherein said at least one acoustic element comprises a property of signal phase and further wherein said signal phase property comprises the phase of the receive signal.

55. The invention of claim 54, wherein said signal phase is controlled for the purpose selected from the group consisting the purposes of beam-steering, signal-mixing and signal-manipulation.

56. An ultrasound transducer comprising:
at least one array of at least one ultrasonic acoustic element, said at least one ultrasonic acoustic element comprising a micro-mechanical ultrasound element, said at least one array arranged in at least one dimension and operative to provide harmonic image information wherein a first bias is provided to said at least one acoustic element during transmit and a second bias different from said first bias is provided to said at least one acoustic element during receive.

57. The ultrasound transducer of claim 56 wherein said micro-mechanical ultrasound element is a capacitive micro-mechanical ultrasound element.

58. An ultrasound system for medical imaging or therapy comprising:
at least one ultrasonic acoustic element, said at least one ultrasonic element operative to transduce between an electrical signal and an acoustic energy;
at least one mirco-mechanical component coupled with said at least one ultrasonic acoustic element, said component comprising
at least one movable mechanical element fabricated on a substrate utilizing at least one integrated circuit manufacturing process;
wherein said at least one micro-mechanical component is operative to manipulate said electrical signal.

59. An ultrasound transducer comprising:
at least one array of at least one ultrasonic acoustic element, said at least one ultrasonic acoustic element operative to transduce between an electrical signal and an acoustic energy; and
at least one micro-mechanical component coupled with said at least one ultrasonic acoustic element, said at least one micro-mechanical component comprising at least one movable mechanical element fabricated on a substrate utilizing integrated circuit manufacturing processes, wherein said at least one micro-mechanical component is operative to manipulate said electrical signal.

* * * * *